United States Patent

Kajino et al.

[11] Patent Number: 5,254,333
[45] Date of Patent: Oct. 19, 1993

[54] HAIR TREATMENT COMPOSITION AND HAIR DYE COMPOSITION

[75] Inventors: Takayoshi Kajino, Chiba; Toru Yoshihara, Tokyo; Joshin Okada, Utsunomiya; Hidetoshi Tagami, Tokyo, all of Japan

[73] Assignee: Kao Corporation, Tokyo, Japan

[21] Appl. No.: 722,517

[22] Filed: Jun. 27, 1991

[30] Foreign Application Priority Data

Jul. 10, 1990 [JP] Japan ................... 2-181759
Sep. 21, 1990 [JP] Japan ................... 2-253378
Sep. 21, 1990 [JP] Japan ................... 2-253379

[51] Int. Cl.⁵ .................................... A61K 7/13
[52] U.S. Cl. ................................ 424/70; 8/404; 8/405; 8/428; 8/429; 8/433; 8/435; 8/580
[58] Field of Search ............ 424/70; 8/404, 428, 8/429, 433, 435, 580, 405

[56] References Cited

U.S. PATENT DOCUMENTS

| | | | |
|---|---|---|---|
| 3,630,654 | 12/1971 | Rosenthal et al. | 8/405 |
| 3,653,797 | 4/1972 | Reiss et al. | 8/10 |
| 3,933,422 | 1/1976 | Saad | 8/580 |
| 3,986,825 | 10/1976 | Sokol | 424/70 |
| 4,517,174 | 5/1985 | Jacquet et al. | 424/70 |
| 4,746,322 | 5/1988 | Herlihy | 8/405 |
| 4,820,308 | 4/1989 | Madrange et al. | 424/70 |
| 4,834,768 | 5/1989 | Grollier | 8/405 |
| 4,996,059 | 2/1991 | Grollier et al. | 8/405 |

*Primary Examiner*—Thurman K. Page
*Assistant Examiner*—Robert H. Harrison
*Attorney, Agent, or Firm*—Birch, Stewart, Kolasch & Birch

[57] ABSTRACT

The hair treatment composition of the present invention comprises (A) 2-benzyloxyethanol and (B) one or more polymers selected from the group consisting of anionic polymers, cationic polymers and amphoteric polymers. The hair dye composition of the present invention comprises (a) an acidic dye, (b) 2-benzyloxyethanol and (C) a water-soluble polymer compound.

2 Claims, No Drawings

HAIR TREATMENT COMPOSITION AND HAIR DYE COMPOSITION

BACKGROUND OF THE INVENTION

1. Field of the Invention

This invention relates to a hair treatment composition. More particularly, it relates to a hair treatment composition showing conditioning effects which can be maintained for a prolonged period of time.

This invention further relates to a hair dye composition which is excellent in dyeing properties, imparts a good feeling to the hair and is highly safe to the hair and the skin.

2. Description of the Prior Art

Hair is damaged, hardened and electrostatically charged due to various physical or chemical treatments, for example shampooing, brushing, drying with a hair dryer, perming or dyeing. In order to maintain beautiful and healthy hair, therefore, it is required to prevent the damage and to soften the hair.

For these purposes, various components have been added to hair cosmetics including rinse and treatment.

In hair treatment and rinse compositions containing a quaternary ammonium salt, a conventional ingredient, the conditioning effect is merely based on the affinity of the quaternary ammonium salt and thus insufficient conditioning is achieved. For example, such a conditioning effect will resist swimming or sweat but is washed out when the hair is washed with a shampoo. This suggests that the conditioning effect of the hair treatment composition is unsatisfactory.

In the case of a shampoo containing a cationized polymer marketed in recent years, mainly a certain/anion complex adsorbs to the surface of the hair and thus the conditioning effects cannot be maintained for a prolonged period of time. When this shampoo is used, furthermore, a treatment with a rinse would rather lose the conditioning effects.

In the case of an oxidation hair dye which has been frequently used, on the other hand, hydrogen peroxide is reacted under alkaline conditions. Thus there is a risk in some cases that the hair is damaged or that primary skin irritation is induced thereby. Therefore attempts have been made to develop a hair dye with the use of an acidic dye which scarcely affects the scalp or the hair. However commercially available hair dyes containing acidic dyes contain benzyl alcohol as a penetration accelerator, which causes some problems regarding dyeing ability or allergy.

Japanese Patent Laid-Open No. 228407/1985 disclosed a hair dye composition comprising a dopa analog, a penetration accelerator and an oxidizing agent. Further, U.S. Pat. No. 3933422 disclosed a hair dye composition comprising a metal-containing dye and a penetration accelerator.

However the hair dye composition described in the aforesaid Japanese Patent is poor in the variation of color tone since the color of the dopa analog is developed only a black tone. Furthermore, the employed oxidant damages the hair.

On the other hand, the hair dye composition described in the aforesaid U.S. patent shows ununiformity in dyeing and poor penetration into the hair. In addition, the metal (chromium or cobalt) employed therein causes some problems from the viewpoints of feeling and safety.

SUMMARY OF THE INVENTION

It is a first object of the present invention to provide a hair treatment composition capable of exerting sufficient conditioning effects, which can be maintained for a prolonged period of time, on the hair.

It is a second object of the present invention to provide a hair dye composition which is excellent in color tone variation and dyeing properties, can impart a good feeling to the hair and is highly safe to the hair and the skin.

In order to achieve the aforesaid first object, the present inventors have studied deeply. As a result, they have discovered that the hair can fully swell when treated with 2-benzyloxyethanol. They have further discovered that its use in the presence of anionic, cationic or amphoteric polymer(s) results in deep penetration of the polymer(s) in the hair, thus exerting conditioning effects on the hair.

The present invention, which has been completed based on the above findings, provides a hair treatment composition which comprises (A) 2-benzyloxyethanol and (B) one or more polymer selected from the group consisting of anionic polymers, cationic polymers and amphoteric polymers.

When the hair is treated with the hair treatment composition of the present invention, the component (A) makes the hair swell and the component (B) penetrates into the hair so as to exert conditioning effect on the hair for a prolonged period of time.

Furthermore, the present inventors have studied deeply and discovered that the aforesaid second object of the present invention can be achieved by providing a composition comprising an acidic dye, a specific penetration accelerator and a specific polymer compound.

The present invention, which has been completed based on the above finding, provides a hair dye composition which comprises (a) an acidic dye, (b) 2-benzyloxyethanol, and (c) a water-soluble polymer compound.

When the hair dye composition of the present invention is applied to the hair and then the hair is washed and dried, the hair dye composition penetrates into the hair and excellently dyes. Simultaneously it imparts moisture and smoothness to the hair.

DETAILED DESCRIPTION OF THE INVENTION

Now the hair treatment composition of the present invention will be first described in detail.

The 2-benzyloxyethanol, which is the component (A) of the hair treatment composition of the present invention, is used in order to promote the swelling of the hair. It may be contained in the composition in an amount of from 0.5 to 50% by weight, preferably from 1 to 30% by weight. When the content of 2-benzyloxyethanol is smaller than the lower limit as specified above, no effect of promoting the swelling of the hair can be achieved. If the content exceeds the upper limit, on the other hand, the effect is not improved any more.

The anionic polymer, which is the component (B) of the hair treatment composition of the present invention, may be either a natural or synthetic one.

Examples of natural anionic polymers include xanthan gum, carrageenan, sodium alginate, pectin, furcellaran, gum arabic, gum ghatti, gum karaya, gum tragacanth and agar powder. In addition, carboxy methylcellulose obtained by carboxymethylation of cellulose is available therefor.

As synthetic anionic polymers, those obtained by polymerizing an acidic vinyl monomer or a salt thereof may be cited. The acidic vinyl monomer means a compound which has an acidic group such as a carboxyl, sulfonate or phosphate group and a polymerizable vinyl group per molecule. Examples thereof include unsaturated monobasic acids such as acrylic, methacrylic, crotonic, vinylbenzoic, 2-acrylamido-2-methylpropanesulfonic, styrenesulfonic, vinylsulfonic, allylsulfonic, methacrylsulfonic, and 3-methacryl-propanesulfonic acids, unsaturated dibasic acids such as itaconic, maleic and fumaric acids and monoesters thereof. In addition, examples of salts thereof include sodium, potassium and ammonium salts thereof.

In the polymerization, another vinyl monomer copolymerizable with the acidic vinyl monomer may be compolymerized as an arbitrary component. However the ratio of said another vinyl monomer should be 60% by mol or below based on the total monomers. Said another vinyl monomer is a monovinyl compound polymerizable with the use of a radical polymerization initiator. Examples thereof include acrylic esters such as methyl acrylate and ethyl acrylate, methacrylic esters such as methyl methacrylate and ethyl methacrylate, styrene compounds such as styrene and -methylstyrene, acrylamide, methacrylamide, vinyl ether and vinyl acetate.

Examples of the cationic polymer, which is the component (B) of the hair treatment composition of the present invention, include cationized cellulose derivatives, cationic starch, cationized guar gum derivatives, diallyl quaternary ammonium salt/acrylamide copolymers, diallyl quaternary ammonium salt polymers, quaterarized polyvinylpyrrolidone derivatives and cationized silicone polymers.

As the aforesaid cationized cellulose derivative, for example, those represented by the following general formula (I) are preferable:

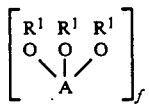 (I)

In the above general formula (I), A represents a residue of an anhydroglucose unit; f is an integer of from 50 to 20,000 and each $R^1$ represents a substituent represented by the following general formula (I-a):

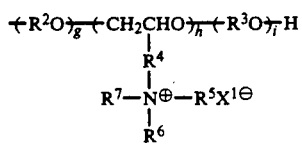 (I-a)

In the above general formula (I-a),
$R^2$ and $R^3$ represent each an alkylene group having 2 or 3 carbon atoms;
g is an integer of from 0 to 10;
h is an integer of from 0 to 3;
i is an integer of from 0 to 10;
$R^4$ represents an alkylene or hydroxyalkylene group having 1 to 3 carbon atoms;
$R^5$, $R^6$ and $R^7$ may be either the same or different from each other and each represents an alkyl, aryl osr aralkyl group having up to 20 carbon atoms or they may form a heterocycle involving the nitrogen atom given in the formula; and $X^1$ is in anion such as a chloride, bromide or iodide or sulfate, sulfonate, methylsulfate, phosphate or nitrate.

The degree of substitution of the aforesaid cationized cellulose derivative ranges from 0.01 to 1. Namely, the average of h per anhydroglucose unit ranges from 0.01 to 1, preferably from 0.02 to 0.5. The average of the sum of g and i ranges from 1 to 3. A degree of substitution of 0.01 or below is insufficient. Although it may exceed 1, it is preferably not more than 1 from the viewpoint of the efficiency of the reaction. It is preferable that $R^5$, $R^6$ and $R^7$ are all methyl groups or that one of them is a long-chain alkyl group having 10 to 18 carbon atoms while the residual ones are short-chain alkyl groups having 1 to 3 carbon atoms. The molecular weight of the cationized cellulose derivative to be used here may preferably range from approximately 100,000 to 8,000,000.

As the aforesaid cationic starch, those represented by the following general formula (II) are preferable:

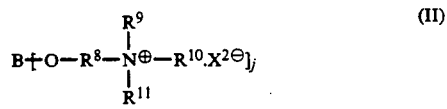 (II)

In the above general formula (II),
B is a starch residue;
$R^8$ represents an alkylene or hydroxyalkylene group;
$R^9$, $R^{10}$ and $R^{11}$ may be either the same or different from each other and each represents an alkyl, aryl or aralkyl group having up to 10 carbon atoms or they may form a heterocycle involving the nitrogen atom given in the formula;
$X^2$ is an anion such as a chloride, bromide or iodide or sulfate, sulfonate, methylsulfate, phosphate or nitrate, and
j is a positive integer.

The degree of substitution of the aforesaid cationic starch ranges from 0.01 to 1. Namely, from 0.01 to 1, preferably from 0.02 to 0.5, cation group is preferably introduced per anhydroglucose unit. A degree of substitution of 0.01 or below is insufficient. Although it may exceed 1, it is preferably not more than 1 from the viewpoint of the efficiency of the reaction.

As the aforesaid cationized guar gum derivative, those represented by the following general formula (III) are preferable:

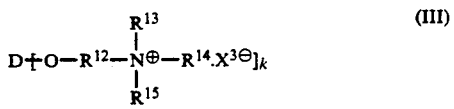 (III)

In the above general formula (III),
D represents a guar gum residue;
$R^{12}$ represents an alkylene or hydroxyalkylene group;
$R^{13}$, $R^{14}$ and $R^{15}$ may be either the same or different from each other and each represents an alkyl, aryl or aralkyl group having up to 10 carbon atoms or they may form a heterocycle involving the nitrogen atom given in the formula;
$X^3$ is an anion such as a chloride, bromide or iodide or sulfate, sulfonate, methylsulfate, phosphate or nitrate; and
k is a positive integer.

The degree of substitution of the aforesaid cationized guar gum derivative ranges from 0.01 to 1. Namely, from 0.01 to 1, preferably from 0.02 to 0.5, cation group is preferably introduced per sugar unit. Cationic polymers of this type are described in, for example, Japanese Patent Publication No. 35640/1983, Japanese Patent Publication No. 46158/1985 and Japanese Patent Laid-Open No. 53996/1983 and marketed under a tradename of Jaguar (a product of Celanese Stein Hall).

As the aforesaid cationic diallyl quaternary ammonium salt polymer and diallyl quaternary ammonium salt/acrylamide copolymer, those represented by the following general formulae (IV) and (V) are preferable:

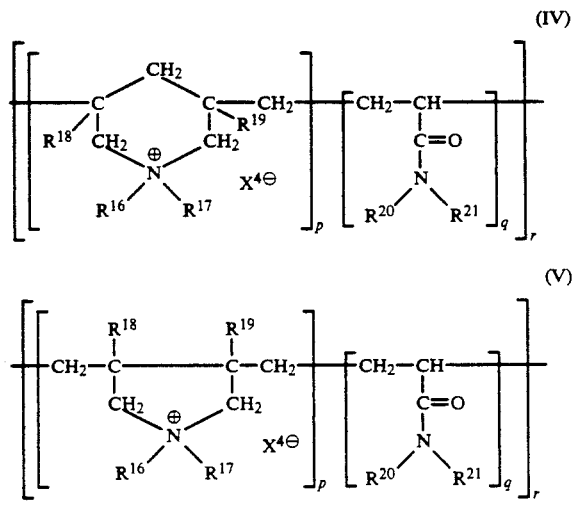

In the above formulae (IV) and (V), $R^{16}$ and $R^{17}$ may be either the same or different from each other and each represents an alkyl (having 1 to 18 carbon atoms), phenyl, aryl, hydroxyalkyl, amidoalkyl, cyanoalkyl, alkoxyalkyl or carboalkoxyalkyl group; $R^{18}$, $R^{19}$, $R^{20}$ and $R^{21}$ may be either the same or different from each other and each represents a hydrogen atom or a lower alkyl (Having 1 to 3 carbon atoms) or phenyl group;

$X^4$ is an anion such as a choloride, bromide or idoide or sulfate, sulfonate, methylsulfate, phosphate or nitrate;

p is an integer of from 1 to 50;
q is an integer of from 0 to 50; and
r is an integer of from 150 to 8000.

The molecular weight of the aforesaid diallyl quaternary ammonium salt/acrylamide copolymer may range from approximately 30,000 to 2,000,000, preferably from 100,000 to 1,000,000.

As the aforesaid quaternarized polyvinylpyrrolidone derivative, those represented by the following general formula (VI) are preferable:

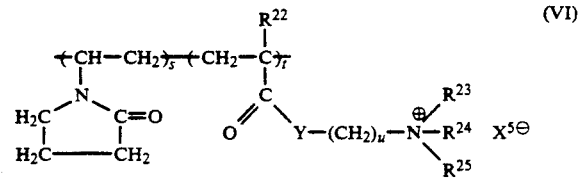

In the above formula (VI), $R^{22}$ represents a hydrogen atom or an alkyl group having 1 to 3 carbon atoms; $R^{23}$, $R^{24}$ and $R^{25}$ may be either the same or different from each other and each represents a hydrogen atom or an alkyl (having 1 to 4 carbon atoms), hydroxyalkyl, amidoalkyl, cyanoalkyl, alkoxyalkyl or carboalkoxyalkyl group;

Y represents an oxygen atom or an NH group in an amide bond;

$X^5$ is an anion such as a chloride, bromide or iodide or sulfate, sulfonate, alkylsulfate having 1 to 4 carbon atoms, phosphate or nitrate;

u is an integer of from 1 to 10; and
s+t is an integer of from 20 to 8,000.

The molecular weight of the aforesaid quaternarized polyvinylpyrrolidone derivative may range from 10,000 to 2,000,000, preferably from 50,000 to 1,500,000.

The content of cationic nitrogen originating from the cationic polymer contained in the vinyl polymer may range from 0.004 to 0.2%, preferably from 0.01 to 0.15%, based on the vinyl polymer. When this content is smaller than 0.004%, no sufficient effects can be achieved. When it exceeds 0.2%, on the other hand, the resulting vinyl polymer is excellent in performance but sometimes undergoes coloration and is also uneconomical.

A typical example of the aforesaid cationic silicone polymer is one represented by the following general formula (VII) and having an average molecular weight of from approximately 3,000 to 100,000). It is described in Cosmetic Ingredient Dictionary (CTFA, U.S.A.) under a name of Amodimethicone.

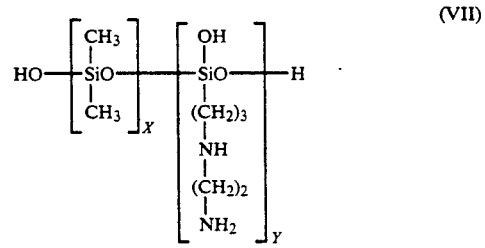

wherein X and Y represent each an integer depending on the molecular weight.

The aforesaid cationic silicone polymer may be preferably used in the form of an aqueous emulsion. The aqueous emulsion may be obtained by, for example, emulsion-polymerizing a cyclic organopolysiloxane with an organodialkoxysilane having an amino alkyl group and a hydroxy, hydroxyalkyl, oxyalkylene or polyoxyalkylene group in the presence of a quaternary ammonium salt surfactant and water in accordance with a method described in Japanese Patent Publication No. 38609/1981.

The amphoteric polymer which is the component (B) of the hair treatment composition of the present invention may b prepared by copolymerizing an acidic vinyl monomer with a basic vinyl monomer; by polymerizing an amphoteric monomer; or by introducing an acidic group, a basic group, an acidic group with a basic group or an amphoteric group into a natural polymer depending on the nature of the natural polymer.

Typical examples of the aforesaid amphoteric polymer will now be described.

(1) Copolymer of Acidic Vinyl Monomer with Basic Vinyl Monomer

A typical example thereof is an amphoteric copolymer obtained by copolymerizing a monomer mixture comprising 45 to 55% by mole of an acidic vinyl monomer or a salt thereof and 45 to 55% by mole of a basic vinyl monomer or a salt thereof in the presence of a known radical polymerization initiator optionally together with a known accelerator at a temperature of 150° C. Each molar ratio as given above corresponds to a case where the vinyl monomer has an acidic or basic group per molecule. It is therefore needed to appropriately adjust the molar ratio so as to control the substantial charge to almost 0, when the monomer has two or more acidic or basic groups per molecule.

An acidic vinyl monomer means a compound which has an acidic group such as a carboxyl, sulfonate or phosphate group and a polymerizable vinyl group per molecule. Examples thereof include unsaturated monobasic acids such as acrylic, methacrylic, crotonic, vinylbenzoic, 2-acrylamido-2-methylpropane-sulfonic, styrenesulfonic, vinylsulfonic, allylsulfonic, methacrylsulfonic and 3-methacryl-propanesulfonic acids unsaturated dibasic acids such as itaconic, maleic and fumaric acids and monoesters thereof. In addition, examples of salts thereof include sodium, potassium and ammonium salts thereof.

A basic vinyl monomer means a compound which has a basic group such as a primary amino, secondary amino or tertiary amino group and a polymerizable vinyl group per molecule. Examples thereof include dimethylaminoethyl methacrylate, diethylaminoethyl methacrylate, dimethylaminoethyl acrylate, diethyliminoethyl acrylate, dimethylaminopropyl acrylate, dimethylaminopropylmethacrylamide, dimethylaminopropylacrylamide, 2-vinylpyridine, 4-vinylpyridine, dimethylallylamine, diallylmethylamine and quaternized derivatives thereof.

The quaternized derivatives involve hydrides, methylated compounds and ethylated compounds wherein the counter anion is, for example, halogen ion such as a chloride or bromide ion, a hydroxide ion or a methylsulfate ion.

In the polymerization, another vinyl monomer copolymerizable with the acidic and basic vinyl monomers may be compolymerized as an arbitrary third component, in addition to the acidic and basic vinyl monomers. However the ratio of said another vinyl monomer should be 60% by mole or below based on the total monomers.

Said another vinyl monomer is a monovinyl compound polymerizable with the use of a radical polymerization initiator. Examples thereof include acrylic esters such as methyl acrylate and ethyl acrylate, methacrylic esters such as methyl methacrylate and ethyl methacrylate, styrene compounds such as styrene and α-methylstyrene, acrylamide, methacrylamide, vinyl ether and vinyl acetate.

(2) Polymer of Amphoteric Monomer

Typical examples thereof are amphoteric polymers obtained by polymerizing an amphoteric monomer represented by the following general formula (VIII) in the presence of a radical polymerization initiator at a temperature of from 20° to 130° C.

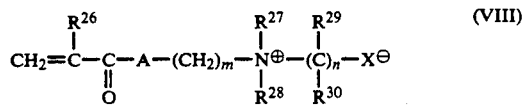
(VIII)

wherein $R^{26}$, $R^{29}$ and $R^{30}$ represent each a hydrogen atom or a methyl group;
wherein $R^{27}$ and $R^{28}$ represent each a methyl or ethyl group;
A is —O— or —NH—;
X is —$CO_2$, —$SO_3$ or —$PHO_3$; and
m and n are each an integer of from 1 to 3.

The amphoteric monomers represented by the general formula (VIII) may be synthesized by reacting an appropriate aminoalkyl acrylate or methacrylate or an aminoalkylamide with a lactone, sultone or cyclic phosphide.

Examples thereof include 3-dimethyl-(methacroyloxyethyl)ammonium propanesulfonate and 3-dimethyl(methacroylamidopropyl)ammonium propanesulfonate.

In the polymerization, another copolymerizable vinyl monomer may be copolymerized as an arbitrary component, in addition to the amphoteric monomer. However the ratio of said another vinyl monomer should be 60% by mol or below based on the total monomers. Said another vinyl monomer is a monovinyl compound polymerizable with the use of a radical polymerization initiator. Examples thereof include acrylic esters such as methyl acrylate and ethyl acrylate, methacrylic esters such as methyl methacrylate and ethyl methacryli esters, styrene compounds such as styrene and α-methylstyrene, acrylamide, methacrylamide, vinyl ether and vinyl acetate.

Either one of the aforesaid anionic, cationic and amphoteric polymers or a combination thereof may be used. The polymer(s) may be preferably used in an amount of from 0.01 to 10% by weight, still preferably from 0.1 to 5% by weight, based on the composition. When the content thereof is smaller than the lower limit as specified above, no noticeable conditioning effects can be achieved. When it exceeds the upper limit, on the other hand, no improvement in the conditioning effects is observed any more.

In order to fully swell the hair so as to achieve desirable effects, it is preferable to adjust the pH value of the hair treatment composition of the present invention within a specific range by adding an acid (C) or an alkali (D) thereto. When an acid, namely, the component (C) is to be added, the pH value of the composition may be preferably adjusted to 2 to 4. When an alkali, namely, the component (D) is to be added, on the other hand, the pH value of the composition may be preferably adjusted to 8.5 to 11. When the pH value of the composition is lower than 2 or exceeds 11, it is afraid that the hair is damaged. Bhat et al. reported the swelling of the hair with an acid or an alkali [G. Ramachandra Bhat et al., J. Soc. Cosmet. Chem., 32, 393–405 (1981)]. Although hydrochloric acid and sodium hydroxide were used in this report respectively as an acid and an alkali, it is preferable in the present invention to use an organic acid as an acid or ammonia or an organic amine as an alkali, since the hair per se is an ion exchanger.

Examples of the aforesaid organic acid include citric, glycolic, succinic, tartaric, lactic, acetic, malic, levulinic, butyric, valeric, oxalic, maleic, fumaric, and mandelic acids. Further, phosphoric acid may be preferably used therefor, though it is not an organic acid.

Examples of the aforesaid organic amines include monoethanolamine, diethanolamine, triethanolamine, aminohydroxymethylpropanediol, 2-amino-2-methyl-1-propanol and 2-amino-methyl-1,3-propanediol. In addition, basic amino acids such as arginine may be used therefor.

Either one of these acids or alkalis or a combination thereof may be used. These compounds may be preferably used in an amount of from 0.3 to 50% by weight, still preferably from 0.5 to 30% by weight, so that the pH value of the composition falls within the range as specified above. When the content thereof is smaller than the lower limit, no swelling effect can be achieved because of the ion-exchanging ability of the hair. When it exceed the upper limit, on the other hand, no improvement in the effect is observed any more.

The hair treatment composition of the present invention may usually comprise the aforesaid components (A), (B) and (C) or (D) and the balance of water.

It is preferable that the hair treatment composition of the present invention contains an organic acid salt such as a sodium or potassium salt of an organic acid salt such as a sodium or potassium salt of an organic acid or an ammonium salt so as to form a buffer system.

The hair treatment composition of the present invention may further contain known direct dye(s) in order to change the color tone of the hair. These direct dyes would deeply penetrate into the hair, similar to the polymers.

Examples of the direct dyes include nitro dyes such as 2-amino-4-hydroxynitrobenzene, 2-amino-5-hydroxynitrobenzene, 2-amino-3-hydroxynitrobenzene, 2-amino-5-N,N-bis-$\beta$-hydroxyethylaminonitrobenzene, 2-amino-4-chloro-5-N-$\beta$-hydroxyethylaminonitorbenzene, 2-amino-4-methyl-5-N-$\beta$-hydroxyethylaminonitrobenzene, 3,4-bis-(N,$\beta$-hydroxyethylamino)nitrobenzene, 2-amino-4-methyl-5N-$\beta$, $\gamma$-dihydroxypropylaminonitrobenzene, 2-amino-4-methyl-5-$\beta$-aminoethylaminonitrobenzene, 2-amino-4-hydroxynitrobenzene; particularly advantageous ones such as 3,4-diaminonitrobenzene, 2,5-diiminonitrobenzene, 2-amino-5-$\beta$-N-hydroxyethylaminonitrobenzene, 2-N-$\beta$-hydroxyethylamino-5-N, N-bis-$\beta$-hydroxyethylaminonitrobenzen, 2-N-methylamino-5-N,N-bis($\beta$-hydroxyethyl)aminonitrobenzene, 2-N-methylamino-5-N-methyl-N-$\beta$-hydroxyethylaminonitrobenzene, 2-N-$\beta$-hydroxyethylamino-5-hydroxynitrobenzene, 3-methoxy-4-N-$\beta$-hydroxyethylaminonitrobenzene, (nitor-4,methylamino-3)phenoxyethano, 2-N-$\beta$-hydroxyethylamino-5-aminonitrobenzene, 2-N-$\beta$-hydroxyethylaminonitrobenzene, 3-amino-N-$\beta$-hydroxyethylaminonitrobenzene, 3-$\beta$-hydroxyethyloxy-4-N-$\beta$-hydroethylaminonitrobenzene, 2-amino-5-N-methylaminonitrobenzene, 2-amino-3-methylnitrobenzene, 2-N-$\beta$-hydroxyethylamino-5-$\beta$, $\gamma$-dihydroxypropyloxynitrobenzene, 3-hydroxy-4-N-$\beta$-hydroxyethylaminonitrobenzene, 3-hydroxy-4-aminonitrobenzene, 2,5-N,N'-$\beta$-hydroxyethylaminonitrobenzene, 2-N-methylamino-4-o-$\beta$, $\gamma$-dihydroxypropyloxynitrobenzene, 2-N-$\beta$-aminoethylamino-5-N,N-bis($\beta$-hydroxyethyl)-aminonitrobenzene, 2-N-$\beta$-aminoethylamino-4-methoxynitrobenzene, 2-N-$\beta$-aminoethylamino-5-$\beta$-hydroxyethyloxynitrobenzene, 1-amino-4-methylaminoanthraquinone, and 1,4-diaminoanthraquinone; acidic dyes such as Red No. 2, Red No. 3, Red No. 102, Red No. 104, Red No. 105, Red No. 106, yellow No. 4, Yellow No. 5, Green No. 3, Blue No. 1, Blue No. 2, Red No. 201, Red No. 227, Red No. 230, Red No. 231, Red No. 232, Orange No. 205, Orange No. 207, Yellow No. 202, Yellow No. 203, Green No. 20., Green No. 204, Green No. 205, Blue No. 202, blue No. 203, Blue No. 205, Brown No. 201, Red No. 401, Red No. 502, Red No. 503, Red No. 504, Red No. 506, Orange No. 402, Yellow No. 402, Yellow No. 403, Yellow No. 406, Yellow No. 407, green No. 401, Green No. 402, Purple No. 401 and Black No. 401; oil-soluble dyes such as Red No. 215, Red No. 218, Red No. 225, Orange No. 201, Orange No. 206, Yellow No. 201, Yellow No. 204, Green No. 202, Purple No. 201, Red No. 501, Red No. 505, Orange No. 403, Yellow No. 404, Yellow No. 405 and Blue No. 403; disperse dyes such as Red No. 215, Red No. 218, Red No. 223, Red No. 225, Orange No. 201, Orange No. 206, Yellow No. 201, Yellow No. 204, Green No. 202, Purple No. 201. Red No. 501, Red No. 505, Yellow No. 404, Yellow No. 405 and Blue No. 403; basic dyes such as Red No. 213, and Red No. 214; and basic dyes manufactured by William Co., such as Sienna Brown, Mahogany, Madder Red, Steel Blue and Straw Yellow.

Furthermore, the hair treatment composition of the present invention may preferably contain various cationic surfactants, amphoteric surfactants, betaine-type surfactants or anionic surfactants in order to form a complex together with the anionic, cationic or amphoteric polymer(s) of the component (B) to thereby modify the feeling to the hair. Either one of these surfactants or a combination thereof may be used.

As the aforesaid cationic surfactants, quaternary ammonium salts represented by the following general formula (IX) are preferable. Examples thereof include stearyltrimethylammonium chloride, distearyldimethylammonium chloride, behenyltrimethylammonium chloride, cetyldimethylbenzylammonium chloride, stearylbenzlmethylammonium chloride, fatty alkyltrimethylammonium, 2-octyldodecyltrimethylammonium chloride, 2-hexyldecyltrimethylammonium chloride and branched dialkyldimethylammonium chloride.

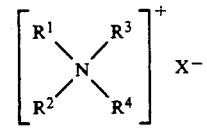

[IX]

wherein one or two of $R^1$, $R^2$, $R^3$ and $R^4$ are each a straight-chain or branched alkyl or hydroxyalkyl group having 8 to 22 carbon atoms and the residual ones are each an alkyl or hydroxyalkyl group having 1 to 3 carbon atoms, a benzyl group or a polyoxyethylene group having up to 10 addition mole number; and X represents a halogen atom or an alkylsulfate group having 1 or 2 carbon atoms.

As the aforesaid amphoteric surfactants, amino acid-type surfactants such as amidoamino acids or acylated amino acids are preferable. As the aforesaid betaine-type surfactants, carbobetaine-type surfactants, sulfobetaine-type surfactants and amidobetaine-type surfactants are preferable.

As examples of surfactants other than those cited above, straight-chain or branched alkyl benzene-sulfonates, alkyl or alkenyl sulfates, alkyl or alkenyl ether sulfates to which ethylene oxide and/or propylene oxide are added, olefin sulfonates, alkane sulfonates, saturated or unsaturated fatty acid salts, alkyl or alkenyl ether carboxylates to which ethylene oxide and/or propylene oxide are added, $\alpha$-sulfo fatty acid salt esters, phosphate type surfactants, sulfosuccinate type surfactants, taurine type surfactants, amide ether sulfate type surfactants and sulfonic acid type surfactants may be cited.

The hair treatment composition of the present invention may further contain solvents, for example, lower alcohols such as ethanol, n-propanol or isopropanol, alkylene glycols such as propylene glycol, dialkylene glycols, trialkylene glycols or alkyl ehters thereof in order to increase the solubility.

Furthermore, the hair treatment composition of the present invention may optionally contain additives commonly employed in the field of cosmetics, for example, thickeners such as hydroxyethylcellulose, conditioning agents such as silicones, perfumes, preservatives, UV absorbers, antioxidants or bactericides, so long as the effects of the present invention are not deteriorated thereby.

After the application of the hair treatment composition of the present invention to the hair, it is preferable to heat the hair at 30° to 45° C. for 10 to 35 minutes so as to get better effects.

The hair treatment composition of the present invention may be used in the form of, for example, hair packing, hair dye, treatment, styling agent, permanent waving agent, hair color, bleaching agent, shampoo or rinse.

Now the hair dye composition of the present invention will be described in detail.

Examples of the acidic dye which is the component (a) of the hair dye composition of the present invention include nitro, azo, nitroso, triphenylmethane, xanthene, quinoline, anthraquinone and indigo dyes. More particularly, those similar to the acidic dyes cited as examples of direct dyes to be used in the aforesaid hair treatment composition of the present invention as the auxiliary component may be employed.

The aforesaid acidic dyes may be preferably used in an amount of from 0.0001 to 10% by weight, still preferably from 0.01 to 1% by weight, based on the composition. When the content thereof is smaller than 0.0001% by weight, sufficient dyeing properties can be hardly achieved. When it exceeds 10% by weight, on the other hand, there is a risk that the solubility is deteriorated. In this case, further, the dyeing properties are scarcely improved with an increase in the content of the dye.

The 2-benzyloxyethanol which is the component (b) of the hair dye composition of the present invention has an effect of increasing the penetration of the aforesaid acidic dye in the hair (i.e., a penetration accelerator). The content of 2-benzyloxyethanol may preferably range from 0.1 to 30% by weight, still preferably from 1 to 10% by weight, based on the composition. When its content is smaller than 0.1% by weight, sufficient dyeing properties can be hardly achieved. When it exceeds 30 % by weight, on the other hand, the solubility of the composition in water is deteriorated and thus a homogeneous liquid phase can be hardly obtained. In this case, further, the dyeing properties are scarcely improved with an increase in the 2-benzyloxyethanol content.

As the water-soluble polymer compound which is the component (c) of the hair dye composition of the present invention, anionic polymers or nonionic polymers are preferable. Examples of such anionic polymers and nonionic polymers include water-soluble cellulosic polymer compounds such as hydroxyethylcellulose, methylcellulose, carboxymethylcellulose and hydroxypropylcellulose; water-soluble gummy polymer compounds such as xanthan gum, guar gum, pullulan, pectin, gum tamariid, gum tragacanth and gum arabic; water-soluble starch polymer compounds such as starches, dextrin, carboxymethylstarch and dialdehyde starch; natural water-soluble polymer compounds such as sodium alginate; and synthetic water-soluble polymer compounds such as polysodium acrylate, carboxyvinylpolymer, polyvinyl alcohol and polyvinylpyrrolidone. Among these compounds, water-soluble cellulosic polymer compounds and water-soluble gummy polymer compounds are particularly preferable.

The content of the aforesaid water-soluble polymer compound in the composition may preferably range from 0.05 to 20% by weight, still preferably from 0.1 to 10% by weight. When this content is smaller than 0.05% by weight, a sufficient flexibility can be hardly imparted to the hair. When this content exceeds 20% by weight, on the other hand, there is a risk that the feeling of the hair is deteriorated.

The pH value of the hair dye composition of the present invention may be preferably adjusted to from 2 to 6, still preferably from 2 to 4. When the pH value thereof is smaller than 2, there is a risk that the hair or the scalp is damaged. When it exceeds 6, on the other hand, the dyeing properties might be deteriorated.

The pH value may be adjusted by using, for example, an organic acid such as lactic, tartaric, acetic, citric or oxalic acid or an inorganic acid such as phosphoric or hydrochloric acid.

The hair dye composition of the present invention may comprise the aforesaid components (a), (b) and (c) and the balance of water. The content of the water may preferably range from 10 to 97% by weight based on the composition.

In addition to the aforesaid essential components, the hair dye composition of the present invention may further contain, for example, lower alcohols, preservatives, chelating agents or perfumes, so long as these additives would not adversely affect the stability of the system and the pH value of the composition.

The hair dye composition of the present invention may be usually provided in the form of a cream, an emulsion, a gel, a solution, a mousse or a foam. The cream, emulsion, gel or solution may be produced by, for example, adding a wetting agent (emulsifier), a solubilizer, a stabilizer, a texture improver, a styling base and/or a perfume, each commonly used in the field of cosmetics, to the hair dye composition of the present invention and processing the resulting mixture in a conventional manner. Examples of the wetting agent (emulsifier) to be used here include anionic, amphoteric and nonionic surfactants such as alkylbenzenesulfonates, aliphatic alcohol sulfates, alkylsulforates, acylated amino acids, aliphatic acid alkanolamides and addition products obtained from ethylene oxide and aliphatic alcohols. Examples of the texture improver and styling base include oily components such as silicone derivatives, higher alcohols and various nonionic surfactants and cationic surfactants.

The mousse or foam may be produced by, for example, adding 1% by weight or below of a common surfactant (nonionic) and 0.5 to 1% by weight of a thickener to the hair dye composition of the present invention and packing the resulting mixture into a aerosol can together with a liquefied propellant such as a fluorocarbon or propane gas in such a manner that the mixture is injected in the form of mousse or foam at the application.

When a keratin fiber such as the hair is to be dyed with the hair dye composition of the present invention, for example, the hair dye composition of the present invention is applied to the keratin fiber at 15° to 50° C.

and then allowed to stand for a certain time (10 to 30 minutes), Next the keratin fiber is washed and dried.

To further illustrate the present invention, the following Examples will be given. Examples 1 to 8 show each an embodiment of the hair treatment composition of the present invention, while Examples 9 to 12 show each an embodiment of the hair dye composition of the present invention.

EXAMPLE 1

Hair treatment compositions of the formulation as specified in Table 1 (invention products 1 to 6 and comparative products 1 and 2) were prepared.

Each hair treatment composition was applied to the hair and the effects thus achieved were evaluated based on the following criteria. Table 1 summarizes the results.

Evaluation Method (1) 4 g of each of the invention products 1 to 6 and comparative products 1 and 2 was applied to 20 g of shampooed tressed (15 cm in length). After allowing to stand at 40° C. for 20 minutes, the tresses were rinsed with running water and dried. The tresses thus treated were referred to as the hair immediately after the treatment. The texture and softness of the hair were evaluated by five skilled panelists based on the following criteria.

1. Feeling of the hair
   - ⊚ : highly smooth and easily combed with fingers,
   - ○ : smooth and easily combed with fingers,
   - Δ: not smooth but somewhat coarse,
   - X: tangled and seriously coarse.
2. Softness of the hair
   - ⊚ : very soft compared with an untreated hair,
   - ○ : soft compared with an untreated hair,
   - Δ: somewhat soft compared with an untreated hair,
   - X: comparable to an untreated hair.

(2) The tresses treated with each of the invention products 1 to 6 and comparative products 1 and 2 were washed with a commercially available shampoo and dried. After repeating this procedure 4 times, the feeling and softness of the hair were evaluated by using un-shampooed ones as controls.

1. Feeling of the hair
   - ○: the same as the control hair,
   - Δ: somewhat inferior to the control hair in flexibility and combability,
   - X: significantly inferior to the control hair in flexibility and combability.
2. Softness of the hair
   - ○ : sufficiently soft similar to the control hair,
   - Δ: somewhat hard compared with the control hair,
   - X: significantly hard compared with the control hair.

TABLE 1

| | | Control | | Invention (formulation : wt. %) | | | | | |
|---|---|---|---|---|---|---|---|---|---|
| | | 1 | 2 | 1 | 2 | 3 | 4 | 5 | 6 |
| 2-benzyloxy-ethanol | | — | 6.0 | 6.0 | 6.0 | 6.0 | 6.0 | 6.0 | 6.0 |
| ethanol | | 30.0 | 30.0 | 30.0 | 30.0 | 30.0 | 30.0 | 30.0 | 30.0 |
| xanthum gum | | 0.15 | — | 0.15 | — | — | 0.15 | 0.15 | 0.15 |
| carboxymethylcellulose | | — | — | — | 0.3 | — | — | — | — |
| Plascize GK-707[1] | | — | — | — | — | 0.3 | — | — | — |
| stearyltrimethylammonium chloride | | 0.3 | 0.3 | 0.3 | 0.3 | 0.3 | 0.3 | 0.3 | — |
| softazoline LPB[2] | | — | — | — | — | — | — | — | 0.3 |
| 90% lactic acid | | 8.0 | 8.0 | 8.0 | 8.0 | 8.0 | — | — | 8.0 |
| sodium lactate | | 1.0 | 1.0 | 1.0 | 1.0 | 1.0 | — | — | 1.0 |
| citric acid | | — | — | — | — | — | 4.0 | — | — |
| sodium citrate | | — | — | — | — | — | 0.1 | — | — |
| monoethanolamine | | — | — | — | — | — | — | 3.0 | — |
| ammonium chloride | | — | — | — | — | — | — | 3.0 | — |
| water | | b[3] | b[3] | b[3] | b[3] | b[3] | b[3] | b[3] | b[3] |
| pH | | 3.5 | 3.5 | 3.5 | 3.5 | 3.5 | 3.5 | 3.5 | 3.5 |
| Immediately after treatment | texture of the hair | ○ | ○ | ⊚ | ⊚ | ⊚ | ⊚ | ⊚ | ⊚ |
| | softness of the hair | ○ | ○ | ⊚ | ⊚ | ⊚ | ⊚ | ⊚ | ⊚ |
| After 4-th run of washing | texture of the hair | X | X | ○ | ○ | ○ | ○ | ○ | ○ |
| | softness of the hair | X | X | ○ | ○ | ○ | ○ | ○ | ○ |

[1] acrylic acid/acrylate/methacrylate copolymer (a product of Goou Kagaku)
[2] N-lauroylamidopropyl betaine (a product of Kawaken Fine Chemicals)
[3] b means the balance.

EXAMPLE 2

A hair peck (pH; 3.5) of the following formulation was produced.

| [Formulation] | (% by weight) |
|---|---|
| xanthan gum | 0.25 |
| stearyltrimethylammonium chloride | 0.5 |
| ethanol | 30.0 |
| 2-benzyloxyethanol | 6.0 |
| sodium lactate | 1.0 |
| lactic acid | 8.0 |
| polyether-modified silicone | 0.5 |
| water | the balance |
| | 100.0 |

4 g of the above hair pack was applied to 20 g of shampooed tresses. After allowing to stand at 40° C. for 20 minutes, the tresses were rinsed with running water and dried. The tresses were highly smooth and soft and could be easily combed with fingers. These effects were sustained after shampooing 4 times.

EXAMPLE 3

A hair dye (ph: 9.2) of the following formulation was produced.

| [Formulation] | (% by weight) |
|---|---|
| xanthan gum | 2.5 |
| stearyltrimethylammonium chloride | 0.5 |
| ethanol | 30.0 |
| 2-benzyloxyethanol | 6.0 |
| ammonium chloride | 3.0 |
| monoethanolamine | 2.0 |
| aqueous ammonia | amount necessary to adjust pH to 9.2 |
| 2,5-diaminonitrobenzene | 0.3 |
| water | the balance |
| | 100.0 |

4 g of the above hair dye was applied to 20 g of shampooed white tresses. After allowing to stand at 40° C. for 20 minutes, the tresses were rinsed with running water and shampooed. Then the white tresses were dyed red. The tresses were highly smooth and soft and could be easily combed with fingers.

EXAMPLE 4

Hair treatment compositions of the formulation as specified in Table 2 (invention products 7 to 13 and comparative products 3 and 4) were prepared.

Each hair treatment composition was applied to the hair and the effects thus achieved were evaluated by the same methods as those described in Example 1. Table 2 summarizes the results.

TABLE 2

(formulation : wt. %)

| | | Control | | Invention | | | | | | |
|---|---|---|---|---|---|---|---|---|---|---|
| | | 3 | 4 | 7 | 8 | 9 | 10 | 11 | 12 | 13 |
| 2-benzyloxy-ethanol | | — | 6.0 | 6.0 | 6.0 | 6.0 | 6.0 | 6.0 | 6.0 | 6.0 |
| ethanol | | 30.0 | 30.0 | 30.0 | 30.0 | 30.0 | 30.0 | 30.0 | 30.0 | 30.0 |
| polymer JR-400[1] | | 0.3 | — | 0.3 | 0.3 | 0.3 | — | — | 0.3 | 0.3 |
| Merquat 100[2] | | — | — | — | — | — | 0.3 | — | — | — |
| Plascize L-401[3] | | — | — | — | — | — | — | 0.3 | — | — |
| softazoline CL[4] | | 0.3 | 0.3 | 0.3 | — | — | 0.3 | 0.3 | 0.3 | 0.3 |
| softazoline LPB[5] | | — | — | — | 0.3 | — | — | — | — | — |
| N-lauroyl-N-methyl taurine | | — | — | — | — | 0.3 | — | — | — | — |
| 90% lactic acid | | 8.0 | 8.0 | 8.0 | 8.0 | 8.0 | 8.0 | 8.0 | — | — |
| sodium lactate | | 1.0 | 1.0 | 1.0 | 1.0 | 1.0 | 1.0 | 1.0 | — | — |
| citric acid | | — | — | — | — | — | — | — | 4.0 | — |
| sodium citrate | | — | — | — | — | — | — | — | 0.1 | — |
| monoethanolamine | | — | — | — | — | — | — | — | — | 3.0 |
| ammonium chloride | | — | — | — | — | — | — | — | — | 3.0 |
| water | | b[6] | b[6] | b[6] | b[6] | b[6] | b[6] | b[6] | b[6] | b[6] |
| pH | | 3.6 | 3.6 | 3.6 | 3.5 | 3.5 | 3.6 | 3.6 | 2.9 | 9.2 |
| Immediately after treatment | texture of the hair | ○ | Δ | ⊙ | ⊙ | ⊙ | ⊙ | ⊙ | ⊙ | ⊙ |
| | softness of the hair | ○ | Δ | ⊙ | ⊙ | ⊙ | ⊙ | ⊙ | ⊙ | ⊙ |
| After 4-th run of washing | texture of the hair | X | X | ○ | ○ | ○ | ○ | ○ | ○ | ○ |
| | softness of the hair | X | X | ○ | ○ | ○ | ○ | ○ | ○ | ○ |

[1] cationized cellulose (a product of Union Carbide)
[2] dimethyldiallyammonium polymer (a product of Merck & Co.)
[3] N-methacryloylethyl-N,N-dimethylammonium-α-N-methylcarboxybetaine polymer (a product Goou Kagau)
[4] 2-cocoyl-N-carboxymethyl-N-hydroxyethylimidazolinium betaine (a product of Kawaken Fine Chemicals)
[5] N-lauroylamidopropyl betaine (a product of Kawaken Fine Chemicals)
[3] b means the balance.

| [Formulation] | (% by weight) |
|---|---|
| Polymer JR-400 | 0.3 |
| N-lauroyl-N-methyltaurine | 0.3 |
| ethanol | 30.0 |
| 2-benzylosxthanol | 8.0 |
| hydroxyethylcellulose | 1.7 |
| sodium lactate | 1.5 |
| lactic acid | 10.0 |
| water | the balance |
| | 100.0 |

4 g of the above hair pack was applied to 20 g of shampooed tresses. After allowing to stand at 40° C. for 20 minutes, the tresses were rinsed with running water and dried. The tresses were highly smooth and soft and could be easily combed with fingers. Theses effects were sustained after shampooing 4 times.

EXAMPLE 6

A hair dye (ph: 9.2) of the following formulation was produced.

| [Formulation] | (% by weight) |
|---|---|
| Merquat 100 | 0.5 |
| Softazôline CL | 1.5 |
| ethanol | 30.0 |
| 2-benzyloxyethanol | 8.0 |
| hydroxyethylcellulose | 1.7 |
| ammonium chloride | 3.0 |
| monoethanolamine | 3.0 |
| 2,5-diaminonitrobenzene | 0.3 |
| water | the balance |
| | 100.0 |

4 g of the above hair dye was applied to 20 g of shampooed white tresses. After allowing to stand at 40° C. for 20 minutes, the tresses were rinsed with running water and shampooed. Then the white tresses were dyed red. The tresses were highly smooth and soft and could be easily combed with fingers.

EXAMPLE 7

A hair dye (ph: 9.0) of the following formulation was produced.

| [Formulation] | (% by weight) |
| --- | --- |
| Merquat 100 | 0.5 |
| N-lauroyl-N-methyltaurine | 1.5 |
| ethanol | 30.0 |
| 2-benzyloxyethanol | 8.0 |
| hydroxyethylcellulose | 1.7 |
| ammonium chloride | 3.0 |
| monoethanolamine | 3.0 |
| Madder Red (a product of Williams) | 0.5 |
| water | the balance |
|  | 100.0 |

4 g of the above hair dye was applied to 20 g of shampooed white tresses. After allowing to stand at 40° C. for 20 minutes, the tresses were rinsed with running water and shampooed. Then the white tresses were dyed red. The tresses were highly smooth and soft and could be easily combed with fingers.

EXAMPLE 8

A hair dye (ph: 8.9) of the following formulation was produced.

| [Formulation] | (% by weight) |
| --- | --- |
| Polymer JR-400 | 0.5 |
| Softazoline LPB | 1.5 |
| ethanol | 30.0 |
| 2-benzyloxyethanol | 8.0 |
| hydroxyethylcellulose | 1.7 |
| ammonium chloride | 4.0 |
| diethanolamine | 4.0 |
| alueous ammonia | amount to necessary to adjust pH to 9.0 |
| 2-amino-5-$\beta$-hydroxyethyl-aminonitrobenzene | 0.5 |
| water | the balance |
|  | 100.0 |

4 g of the above hair dye was applied to 20 g of shampooed white tresses. After allowing to stand at 40° C. for 20 minutes, the tresses were rinsed with running water and shampooed. Then the white tresses were dyed red. The tresses were highly smooth and soft and could be easily combed with fingers.

As these Examples show, the hair treatment compositions of the present invention can exert sufficient conditioning effects on the hair and these effects can be sustained for a prolonged period of time.

EXAMPLE 9

| [Formulation] | (% by weight) |
| --- | --- |
| Black No. 401 | 0.5 |
| ethanol | 10 |
| carboxymethylcellulose | 1.0 |
| penetration accelerator (specified in Table 3) | 7.0 |
| water | the balance |
|  | 100.0 |

The pH value of the mixture of the above formulation was adjusted to 4 with a lactate buffer solution. Thus the hair dye compositions (invention products 14 and comparative products 1 to 3) were obtained.

Each hair dye composition was applied to gray human tresses and allowed to stand at 30° C. for 30 minutes. Then the tresses were washed with a common shampoo and dried. The dyeing properties and the flexibility of the treated hair were sensorially evaluated. Table 3 shows the results.

TABLE 3

| Hair dye composition | | Penetration accelerator | Dyeing properties | Flexibility of the hair |
| --- | --- | --- | --- | --- |
| Invention 1 | | 2-benzyloxyethanol | ⊚ | ○ |
| Comparative | 1 | benzyl alcohol | ○ | X |
| | 2 | diethylene glycol monoethyl ether | X | ○ |
| | 3 | none | X | X |

⊚ : very good,
○ : good,
△ : moderate,
X: poor.

EXAMPLE 10

The pH values of mixtures of the formulation as specified in Table 4 were adjusted to 3 with a lactate/citrate buffer solution to thereby give hair dye compositions (invention products 2 and 3). By using these hair dye compositions, the dyeing properties and the flexibility of the hair were evaluated in the same manner as the one described in example 9. Table 4 shows the results.

TABLE 4

| | | Formulation (% by weight) | |
| --- | --- | --- | --- |
| | | 2 | 3 |
| acidic dye | Orange No. 205 | 0.2 | — |
| | Purple No. 401 | — | 0.2 |
| ethanol | | 20 | 20 |
| water-soluble polymer compound | xanthan gum | 1.0 | — |
| | hydroxyethylcellulose | — | 1.0 |
| 2-benzyloxyethanol | | 5.0 | 5.0 |
| water | | the balance | the balance |
| Dyeing properties | | ⊚ | ⊚ |
| Flexibility of the hair | | ○ | ○ |

EXAMPLE 11

| [Formulation] | (% by weight) |
| --- | --- |
| Black No. 401 | 0.1 |
| Purple No. 401 | 0.1 |
| ethanol | 20 |
| hydroxyethylcellulose | 0.5 |
| 2-benzyloxyethanol | 10 |
| amphoteric surfactant (softazoline CL) (a product of Kawaken Fine Chemicals) | 0.3 |
| water | the balance |
| perfume | q.s. |
|  | 100.0 |

The pH value of the mixture of the above formulation was adjusted to 2.8 with a citric acid/sodium citrate buffer solution to thereby give a black hair dye composition. When the hair was dyed with this hair dye composition, excellent dyeing properties and a good texture of the dyed hair were achieved.

EXAMPLE 12

| [Formulation] | (% by weight) |
| --- | --- |
| Purple No. 401 | 0.07 |
| Orange No. 205 | 0.2 |
| Red No. 204 | 0.01 |
| Black No. 401 | 0.03 |
| ethanol | 15 |
| hydroxyethylcellulose | 1.5 |
| 2-benzyloxyethanol | 5 |
| 1,3-butanediol | 5 |
| water | the balance |
| perfume | q.s. |
| | 100.0 |

The pH value of the mixture of the above formulation was adjusted to 3.3 with a citric acid/sodium citrate buffer solution to thereby give a brown hair dye composition. When the hair was dyed with this brown hair dye composition, excellent dyeing properties and a good texture of the dyed hair were achieved.

As these Examples show, the hair dye compositions show a wide variation in color tone, are excellent in dyeing properties, impart a good touch to the hair and are highly safe to the hair and the skin.

What is claimed is:

1. A hair dye composition which comprises (a) 0.0001 to 10% by weight of an acidic dye, (b) 0.1 to 30% by weight of 2-benzyloxyethanol, and (c) 0.05 to 20% by weight of a water-soluble nonionic polymer compound.

2. A hair dye composition as claimed in claim 1, which further comprises an acid and has a pH value of from 2 to 6.

* * * * *